(12) United States Patent
Ding et al.

(10) Patent No.: US 9,019,483 B2
(45) Date of Patent: Apr. 28, 2015

(54) METHOD TO EXTEND SINGLE WAVELENGTH ELLIPSOMETER TO OBTAIN SPECTRA OF REFRACTIVE INDEX

(71) Applicant: Intermolecular Inc., San Jose, CA (US)

(72) Inventors: Guowen Ding, San Jose, CA (US); Brent Boyce, Novi, MI (US); Mohd Fadzli Anwar Hassan, San Francisco, CA (US); Minh Huu Le, San Jose, CA (US); Zhi-Wen Wen Sun, Sunnyvale, CA (US); Yu Wang, San Jose, CA (US)

(73) Assignee: Intermolecular, Inc., San Jose, CA (US)

( * ) Notice: Subject to any disclaimer, the term of this patent is extended or adjusted under 35 U.S.C. 154(b) by 0 days.

(21) Appl. No.: 13/727,854

(22) Filed: Dec. 27, 2012

(65) Prior Publication Data

US 2014/0185034 A1 Jul. 3, 2014

(51) Int. Cl.
*G01N 21/41* (2006.01)

(52) U.S. Cl.
CPC .................................. *G01N 21/4133* (2013.01)

(58) Field of Classification Search
USPC ............................................................ 356/72
See application file for complete search history.

(56) References Cited

U.S. PATENT DOCUMENTS

2005/0164412 A1* 7/2005 Beck et al. ...................... 438/1

OTHER PUBLICATIONS

Santiago, L., et al.; Spectroscopic Ellipsometry; University of Texas at El Paso; University of Texas at El Paso.

* cited by examiner

*Primary Examiner* — Abdullahi Nur

(57) ABSTRACT

Methods are provided to use data obtained from a single wavelength ellipsometer to determine the refractive index of materials as a function of wavelength for thin conductive films. The methods may be used to calculate the refractive index spectrum as a function of wavelength for thin films of metals, and conductive materials such as conductive metal nitrides or conductive metal oxides.

13 Claims, 11 Drawing Sheets

METHOD TO EXTEND SINGLE WAVELENGTH ELLIPSOMETER TO OBTAIN SPECTRA OF REFRACTIVE INDEX

FIELD OF THE INVENTION

The present invention relates generally to a diagnostic method for determining physical and optical properties of a deposited material.

BACKGROUND OF THE INVENTION

Spectroscopic ellipsometry (SE) is a powerful technique for determining a wide variety of optical and physical properties of materials. The full spectra of the ellipsometric parameters Δ and Ψ as a function of wavelength from the ultraviolet region (UV) (wavelengths in the range of between about 10 nm and about 400 nm) to the infra-red region (IR) (wavelengths in the range of about 700 nm to about 300 µm) can be determined with a high degree of precision and accuracy in a few seconds. In practice, most commercial SE systems collect data between about 140 nm and about 2000 nm. Such data can also be processed to provide (i) the values of the dielectric functions (i.e. the real and the imaginary parts of the optical dielectric constant as a function of wavelength) of semiconductors, metals, and wide band gap materials; (ii) depth-profiles of interfaces, thin films, and multilayer structures with almost atomic resolution; (iii) the composition for any layers (bulk, interface, or surface) that are composites or alloys; (iv) the micro-roughness of the surface layer; and (v) the true near-surface temperature of samples in the process chamber when used as an in-situ diagnostic tool. Furthermore, the results discussed above obtained by SE are reliable and trustworthy, with excellent corroboration with independent results of cross-sectional transmission electron microscopy (XTEM), Rutherford backscattering spectrometry (RBS), and atomic force microscopy (AFM) studies on the same multilayer structures. However, the spot size (e.g. the sample area) of spectroscopic ellipsometers is large compared to single wavelength ellipsometers. Additionally, the cost of spectroscopic ellipsometers exceeds that of single wavelength ellipsometers.

It is desirable to develop methods that would allow the refractive index of materials to be determined as a function of wavelength based on single wavelength ellipsometer data.

SUMMARY OF THE DISCLOSURE

In some embodiments, data obtained from a single wavelength ellipsometer is used to determine the refractive index of materials to be determined as a function of wavelength for thin conductive films.

BRIEF DESCRIPTION OF THE DRAWINGS

To facilitate understanding, identical reference numerals have been used, where possible, to designate identical elements that are common to the figures. The drawings are not to scale and the relative dimensions of various elements in the drawings are depicted schematically and not necessarily to scale.

The techniques of the present invention can readily be understood by considering the following detailed description in conjunction with the accompanying drawings, in which.

DETAILED DESCRIPTION

A detailed description of one or more embodiments is provided below along with accompanying figures. The detailed description is provided in connection with such embodiments, but is not limited to any particular example. The scope is limited only by the claims and numerous alternatives, modifications, and equivalents are encompassed. Numerous specific details are set forth in the following description in order to provide a thorough understanding. These details are provided for the purpose of example and the described techniques may be practiced according to the claims without some or all of these specific details. For the purpose of clarity, technical material that is known in the technical fields related to the embodiments has not been described in detail to avoid unnecessarily obscuring the description.

The optical properties (e.g. refractive index (n) and extinction coefficient (k)) can be used to determine other useful properties about the film such as thickness, composition, micro-roughness, and the like. Often, the optical properties will vary with wavelength, thereby requiring the use of a spectroscopic ellipsometer to determine the optical properties. However, it would be beneficial to allow the use of data from a single wavelength ellipsometer to be extended to calculate or estimate the optical properties across a range of wavelengths.

Figure 1:
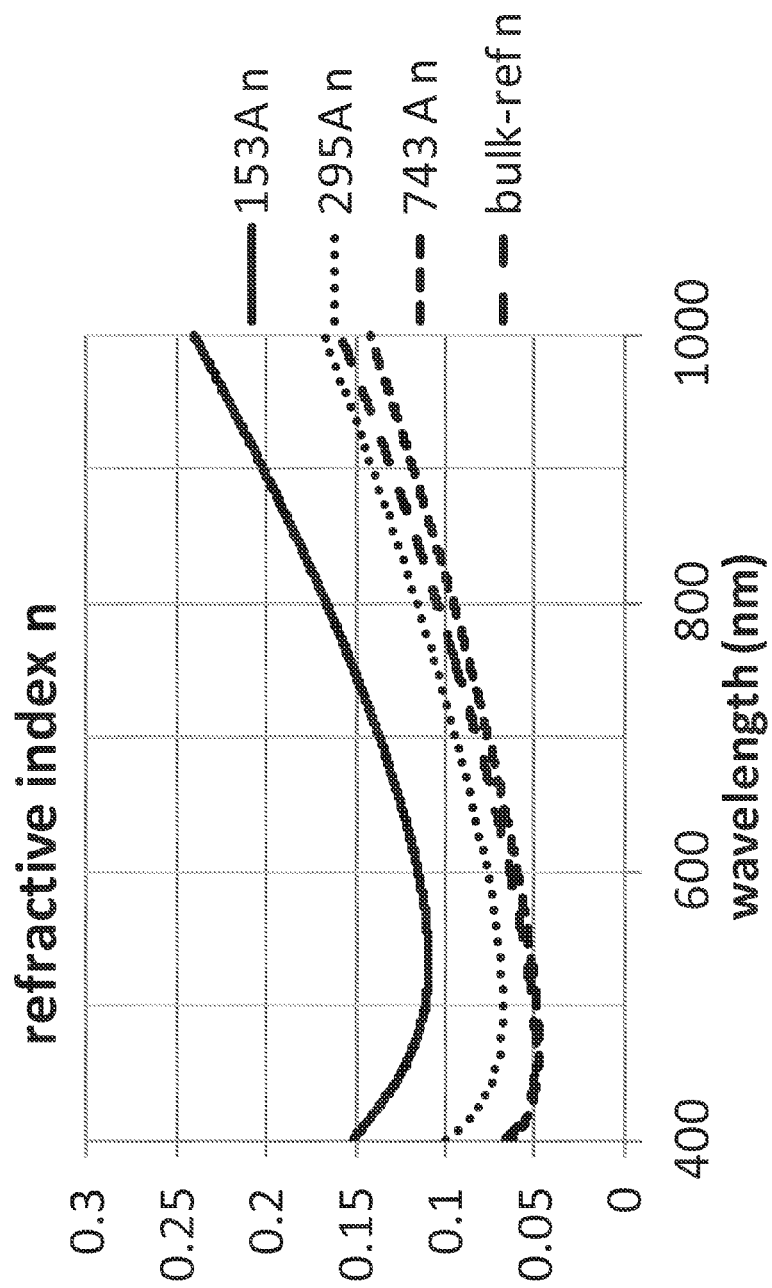
FIG. 1 presents data for the refractive index (n) versus wavelength determined using a spectroscopic ellipsometer for three thicknesses of Ag.

FIG. 1 presents data for the refractive index (n) versus wavelength determined using a spectroscopic ellipsometer for three thicknesses of Ag. The data indicate that the refractive index decreases as the thickness of the Ag layer increases. Additionally, the data indicate that the refractive index increases at longer wavelengths. These data illustrate the general need to use a spectroscopic ellipsometer to determine the optical properties.

Figure 2:
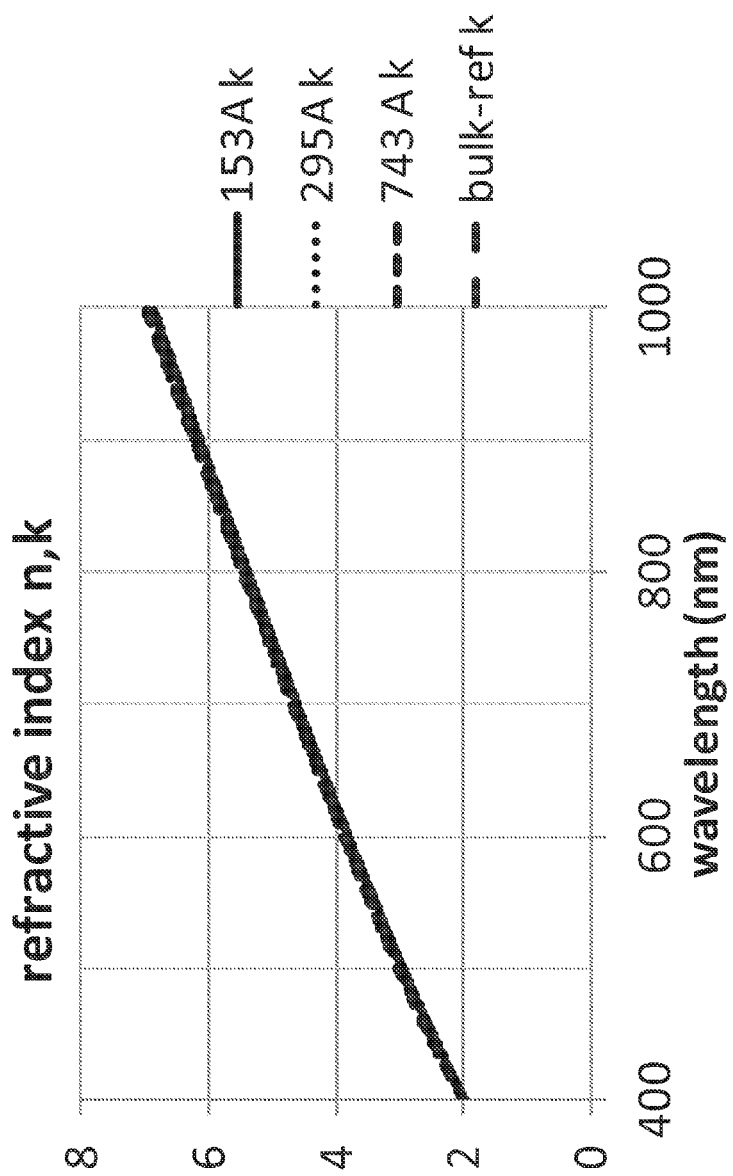
FIG. 2 presents data for the extinction coefficient (k) versus wavelength determined using a spectroscopic ellipsometer for three thicknesses of Ag.

FIG. 2 presents data for the extinction coefficient (k) versus wavelength determined using a spectroscopic ellipsometer for three thicknesses of Ag. The data indicate that the extinction coefficient is essentially constant as the thickness of the Ag layer increases. Additionally, the data indicate that the extinction coefficient increases at longer wavelengths. These data illustrate the general need to use a spectroscopic ellipsometer to determine the optical properties. Note that the absolute value of k is much greater than n.

The dielectric constant of a material can be related to the optical properties as indicated in Eqn 1. Further, the dielectric constant of a material can be expressed as a function of the permittivity of a material as given in Eqn 2.

$$\in = (n+ik)^2 \qquad \text{Eqn 1.}$$

$$\in = \in_1 + i\in_2 \qquad \text{Eqn 2.}$$

Where $\in$ is the dielectric constant, n is the refractive index, k is the extinction coefficient, $\in_1$ is the real part of the absolute permittivity, and $\in_2$ is the imaginary part of the absolute permittivity.

Figure 3:
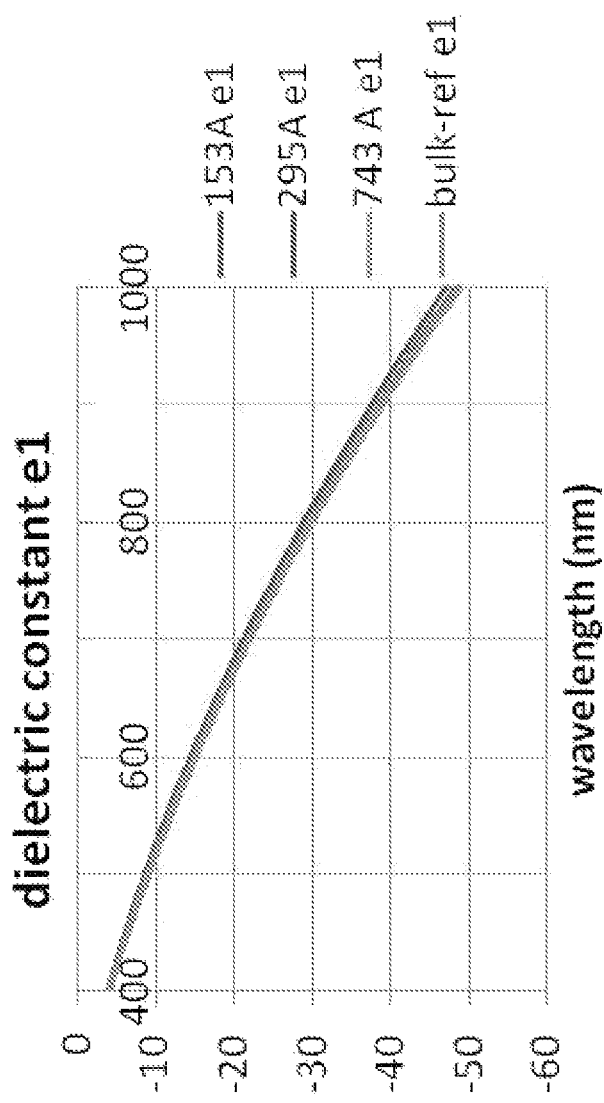
FIG. 3 presents data for the real part of the dielectric constant $\in_1$ versus wavelength calculated from the refractive index (n) and the extinction coefficient (k) versus wavelength data from FIG. 1 and FIG. 2 for three thicknesses of Ag.

FIG. 3 presents data for the real part of the dielectric constant $\in_1$ versus wavelength calculated from the refractive index (n) and the extinction coefficient (k) versus wavelength data from FIG. 1 and FIG. 2 for three thicknesses of Ag. The data indicate that the real part of the dielectric constant $\in_1$ is essentially constant as the thickness of the Ag layer increases (similar to the extinction coefficient). Additionally, the data indicate that the real part of the dielectric constant $\in_1$ decreases at longer wavelengths.

Figure 4:
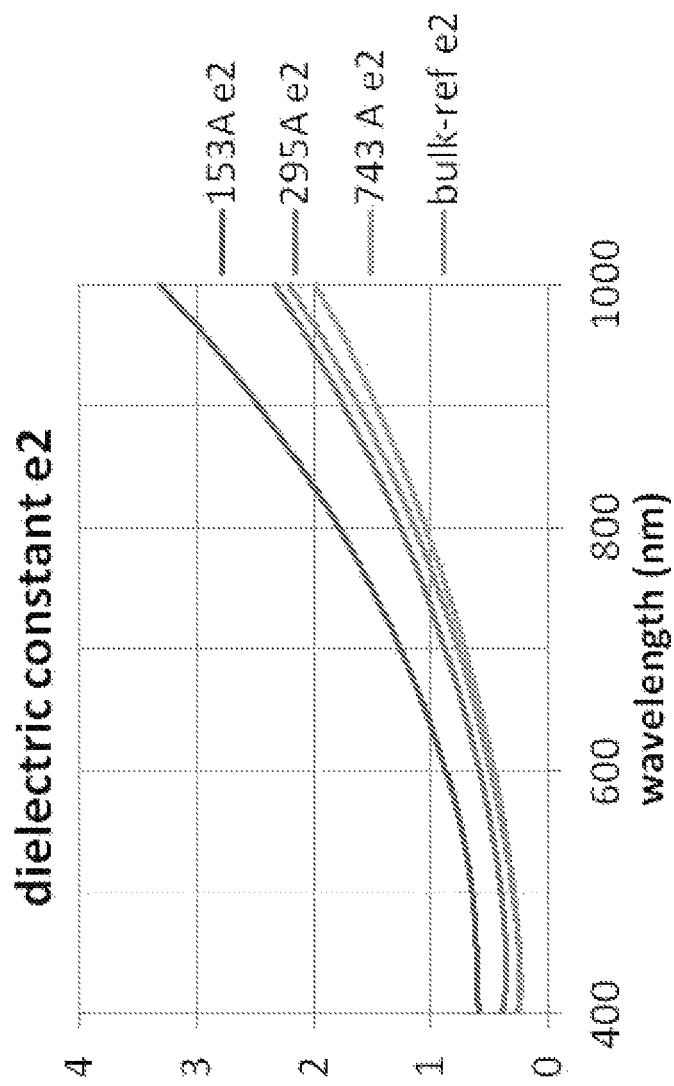
FIG. 4 presents data for the dielectric constant $\in_2$ versus wavelength calculated from the refractive index (n) and the extinction coefficient (k) versus wavelength data from FIG. 1 and FIG. 2 for three thicknesses of Ag.

FIG. 4 presents data for the imaginary part of the dielectric constant $\in_2$ versus wavelength calculated from the refractive index (n) and the extinction coefficient (k) versus wavelength data from FIG. 1 and FIG. 2 for three thicknesses of Ag. The data indicate that the imaginary part of the dielectric constant $\in_2$ increases as the thickness of the Ag layer increases. Additionally, the data indicate that the imaginary part of the dielectric constant $\in_2$ increases at longer wavelengths. Note that the absolute value of $\in_1$ is much greater than $\in_2$.

Figure 5:
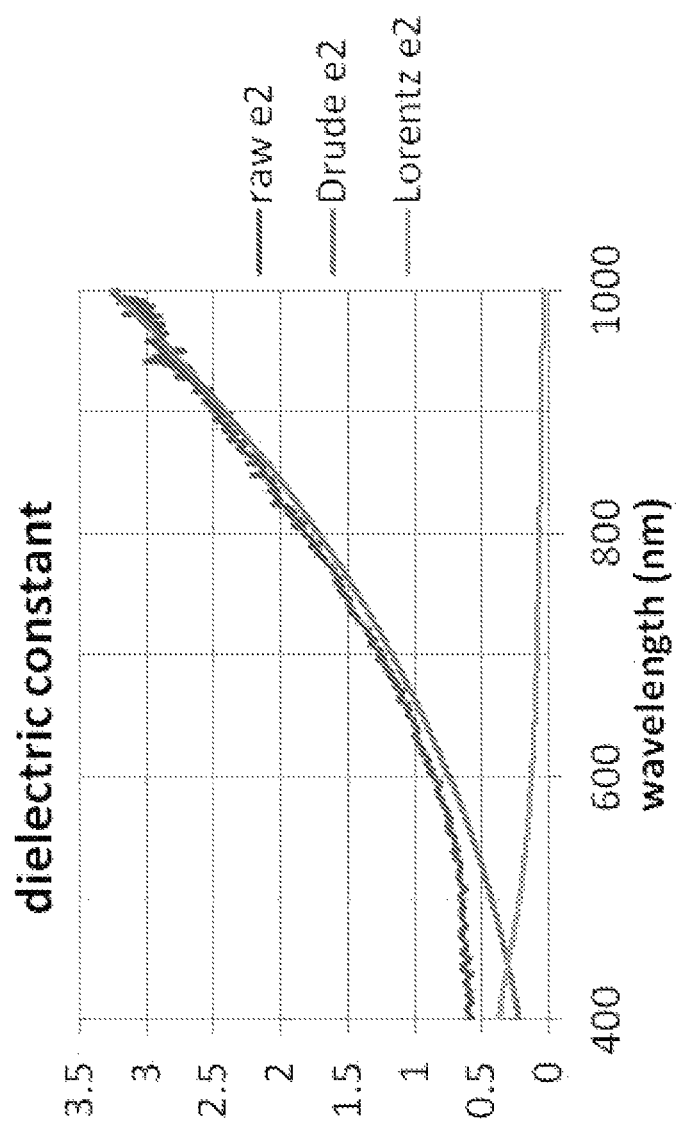
FIG. 5 presents data for the dielectric constant versus wavelength data comparing the fit of the Drude model and the Lorentz model with experimental data for a Ag film with a thickness of 153 Å.
Figure 6:
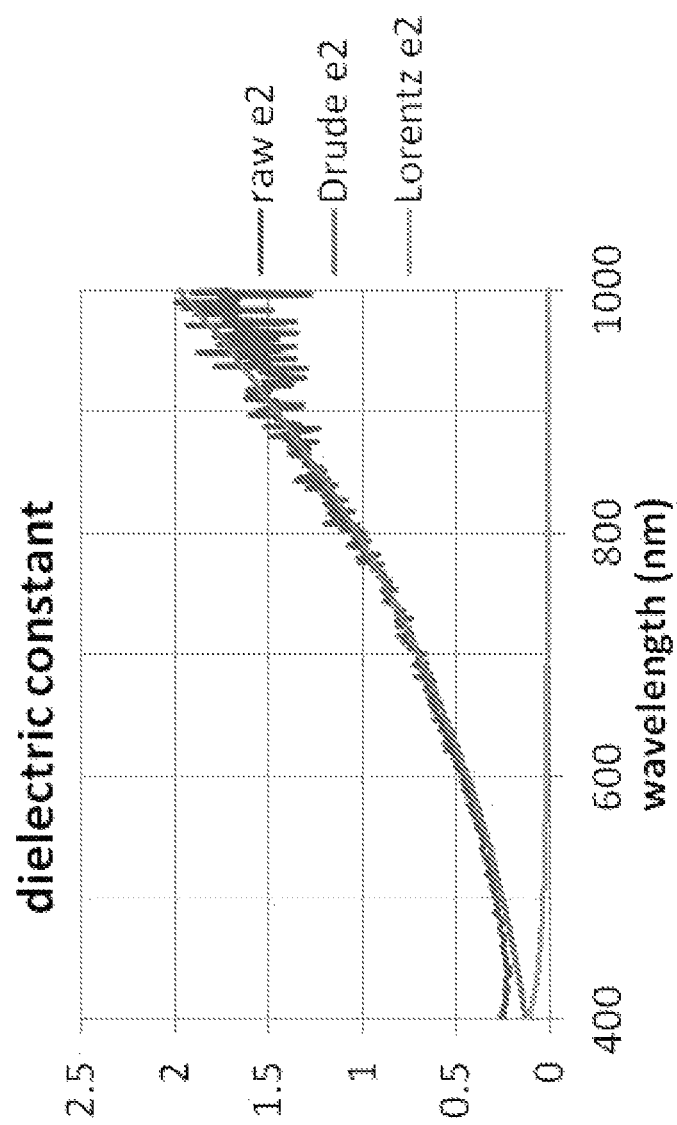
FIG. 6 presents data for the dielectric constant versus wavelength data comparing the fit of the Drude model and the Lorentz model with experimental data for a Ag film with a thickness of 743 Å.

The Drude model, discussed below, can be used to estimate the imaginary part of the dielectric constant $\in_2$ versus wavelength as illustrated in FIGS. 5 and 6. Those skilled in the art will understand that the Drude model was developed to describe the transport properties of electrons through materials, especially highly conductive materials such as metals. Examples of metals of interest include silver, titanium, tantalum, platinum, ruthenium, nickel, and tungsten. Other conductive materials may include conductive compounds such as conductive metal nitrides, conductive metal oxides, and the like. Examples of conductive metal nitride materials include titanium nitride, tantalum nitride, tungsten nitride, molybdenum nitride, and vanadium nitride. Examples of conductive metal oxide materials include molybdenum oxide, indium tin oxide, tin oxide, ruthenium oxide, and zinc oxide. FIG. 5 presents data for the dielectric constant versus wavelength data comparing the fit of the Drude model and the Lorentz model with experimental data for a Ag film with a thickness of 153 A. These data indicate that the Drude model fits the experiments data satisfactorily for wavelengths greater than about 550 nm. FIG. 6 presents data for the dielectric constant versus wavelength data comparing the fit of the Drude model and the Lorentz model with experimental data for a Ag film with a thickness of 743 A. These data indicate that the Drude model fits the experiments data satisfactorily for wavelengths greater than about 450 nm (i.e. over a greater wavelength range). The data presented in FIGS. 5 and 6 indicate that the Drude model can be used for thicker films to calculate useful properties.

An expression for the Drude model is given in Eqn. 3.

$$\tilde{\varepsilon}(\lambda) = \varepsilon_\infty - \frac{i4\pi\hbar^2}{\rho(\hbar\lambda + i\lambda^2\tau)} \qquad \text{Eqn. 3}$$

Where $\in(\lambda)$ is the permittivity, $\in_\infty$ is the residual dielectric response from the inter-band transitions, $\hbar$ is Planck's constant, $\rho$ is the resistivity, $\tau$ is the electron scattering time, and $\lambda$ is the wavelength.

Figure 7:
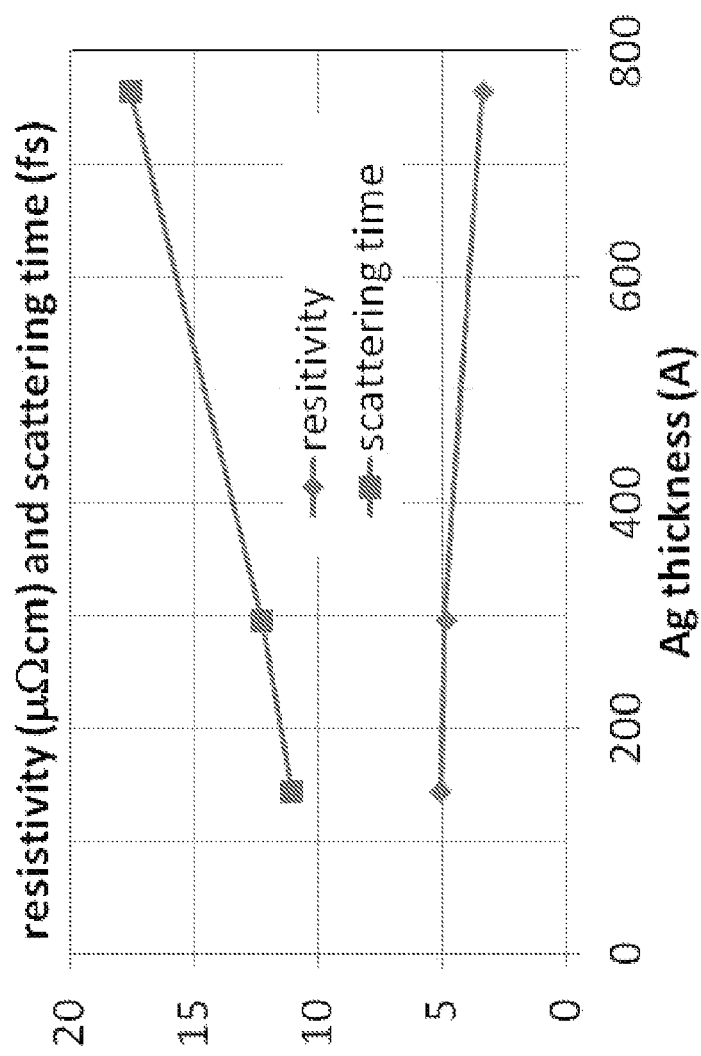
FIG. 7 presents calculated data for resistivity and scattering time versus Ag layer thickness based on the Drude model.

FIG. 7 presents calculated data for resistivity and scattering time versus Ag layer thickness based on the Drude model using refractive index and extinction coefficient data as collected with respect to FIGS. 1 and 2. The data in FIG. 7 indicated that as the thickness of the Ag film increases, the longer the electron scattering time and the lower the resistivity. Over these wavelengths, the product ($\tau \times \rho$) is approximately a constant (i.e. the product is 56.5 at a thickness of 153 A, 60.3 at a thickness of 295 A, and 59.8 a thickness of 763 A).

Equation 2 can be rewritten as indicated in Eqn. 4.

$$\varepsilon = \varepsilon_\infty - \frac{\tau\hbar^2}{\varepsilon_0\rho(\tau^2 \cdot E^2 + \hbar^2)} + i\frac{\hbar^2}{E\varepsilon_0\rho(\tau^2 \cdot E^2 + \hbar^2)} \qquad \text{Eqn. 4}$$

Where E is the photon energy (i.e. $\hbar\omega = \hbar c/\lambda$) and the other variables are as indicated previously, c is the speed of light. This expression describes the dielectric constant as a function of resistivity ($\rho$) and electron scattering time ($\tau$). From Eqns. 1 and 2, the refractive index (n) and the extinction coefficient (k) can be expressed as functions of the dielectric constant as given by Eqns. 5 and 6.

$$n = \sqrt{0.5[(\varepsilon_1^2 + \varepsilon_2^2)^{0.5} + \varepsilon_1]} \qquad \text{Eqn. 5}$$

$$k = \sqrt{0.5[(\varepsilon_1^2 + \varepsilon_2^2)^{0.5} - \varepsilon_1]} \qquad \text{Eqn. 6}$$

As discussed previously, since $|\in_1| \gg |\in_2|$, n can be simplified as indicated in Eqn. 7.

$$n \approx \frac{\rho}{2\varepsilon_0(\rho\tau)^2\omega^3 k} = \frac{\rho}{X\omega^3 k} \qquad \text{Eqn. 7}$$

Where X is a constant and $\omega = c/\lambda$.

The resistivity ($\rho$) can be obtained from a 4-point probe measurement of the film. As indicated in FIG. 2, the extinction coefficient (k) is not sensitive to the thickness of the film and can be approximated by the bulk value which is easily obtained from a handbook or other suitable reference. The constant (X) can be determined from a measurement of n, k, and $\rho$ at a single wavelength (i.e. by using s single wavelength ellipsometer). Once these values have been determined at one wavelength, the spectrum of n and k (and other useful properties) can be calculated as a function of wavelength across the useful range of wavelengths between 400 nm and 1000 nm.

Figure 8:
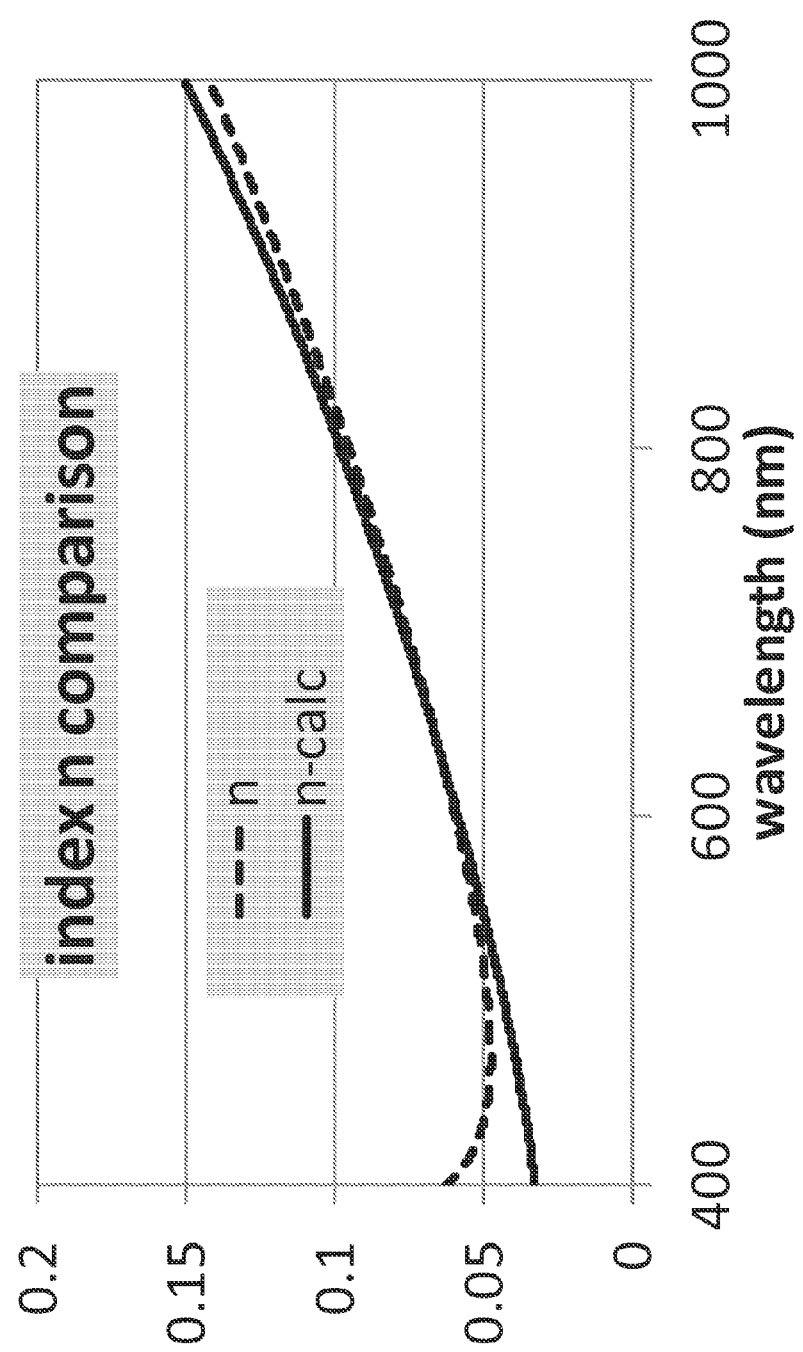
FIG. 8 presents calculated data for refractive index (n) versus wavelength for a Ag film with a thickness of 740 Å.

FIG. 8 presents calculated data for refractive index (n) versus wavelength for a Ag film with a thickness of 740 A compared to experimental data obtained using a spectroscopic ellipsometer. The data were normalized at a wavelength of 632.8 nm. The data were calculated using the equations and assumptions discussed previously. The data indicate that the model provides a good estimation of the refractive index over wavelengths between about 500 nm and 1000 nm.

Figure 9:
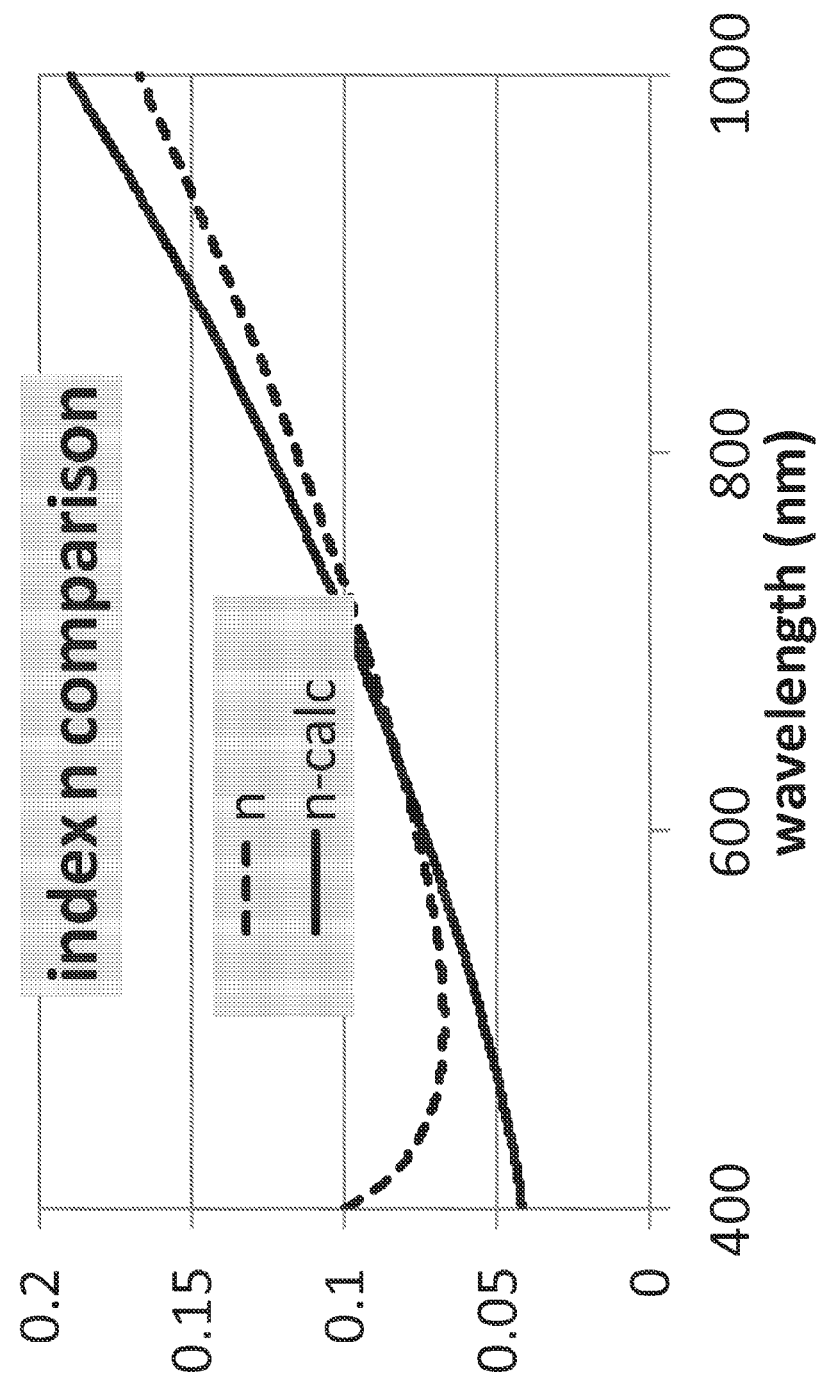
FIG. 9 presents calculated data for refractive index (n) versus wavelength for a Ag film with a thickness of 300 Å.

FIG. 9 presents calculated data for refractive index (n) versus wavelength for a Ag film with a thickness of 300 Å compared to experimental data obtained using a spectroscopic ellipsometer. The data were normalized at a wavelength of 632.8 nm. The data were calculated using the equations and assumptions discussed previously. The data indicate that the model provides a good estimation of the refractive index over wavelengths between about 500 nm and 1000 nm, although the agreement is not as good as for the thicker film.

Figure 10:
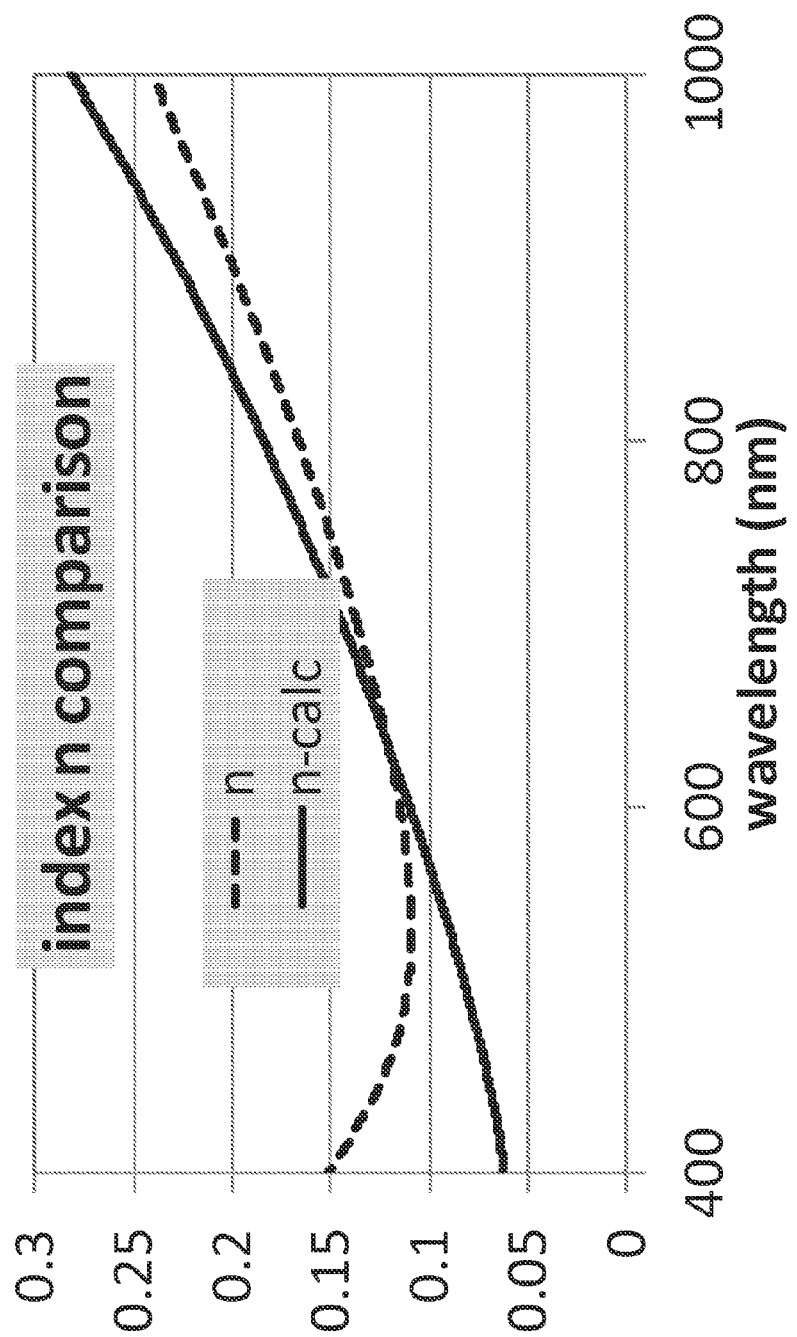
FIG. 10 presents calculated data for refractive index (n) versus wavelength for a Ag film with a thickness of 150 Å.

FIG. 10 presents calculated data for refractive index (n) versus wavelength for a Ag film with a thickness of 150 Å compared to experimental data obtained using a spectroscopic ellipsometer. The data were normalized at a wavelength of 632.8 nm. The data were calculated using the equations and assumptions discussed previously. The data indicate that the model provides a reasonable estimation of the refractive index over wavelengths between about 500 nm and 1000 nm. The agreement between the data and the model in FIG. 10 is about 20%. This level of agreement may be acceptable for many of the properties of interest for thin films.

Figure 11:
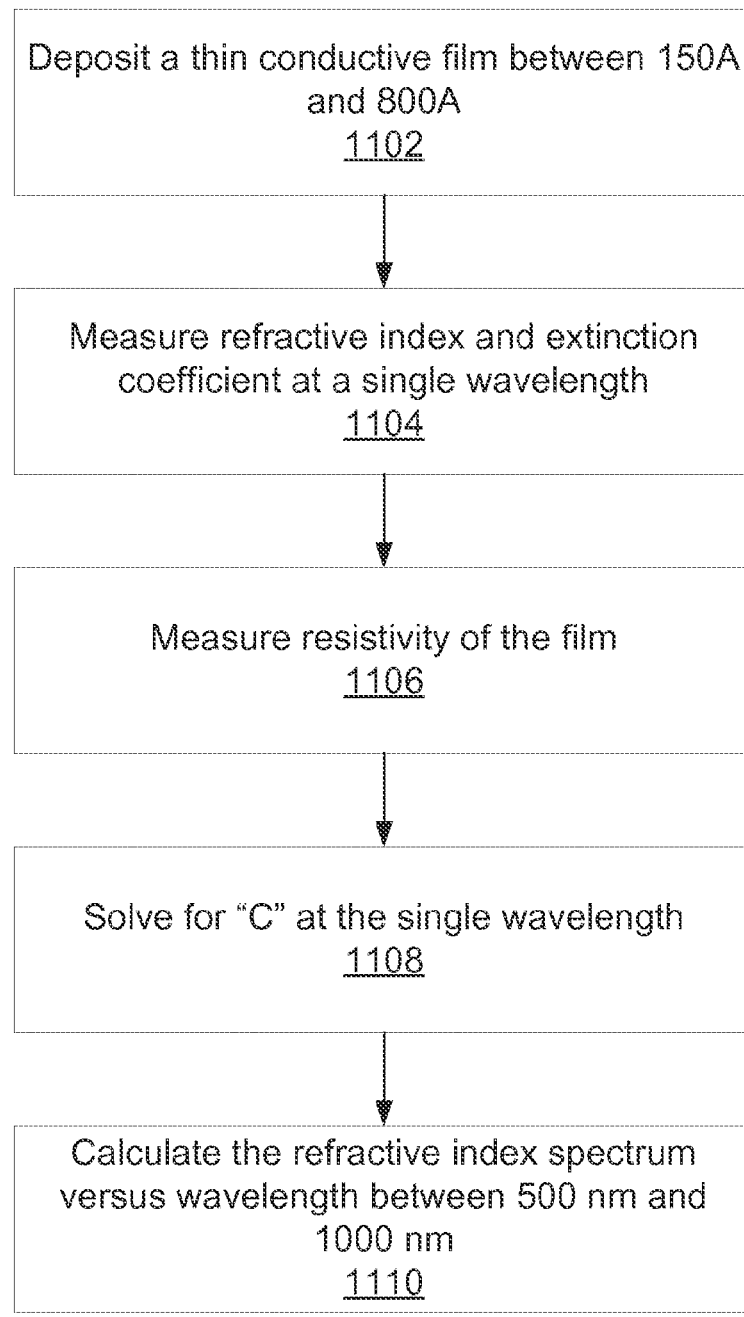
FIG. 11 presents a flow chart for methods according to some embodiments.

FIG. 11 presents a flow chart for methods according to some embodiments. In step 1102, a conductive thin film with a thickness between 150 Å and 800 Å is deposited on a substrate. As discussed previously, the thin film must be a metal or a highly conductive material. Those skilled in the art will recall that the Drude model was developed to describe the transport properties of electrons through materials, especially highly conductive materials such as metals. Examples of metals of interest include silver, titanium, tantalum, platinum, ruthenium, nickel, and tungsten. Other conductive materials may include conductive compounds such as conductive metal nitrides, conductive metal oxides, and the like. Examples of conductive metal nitride materials include titanium nitride, tantalum nitride, tungsten nitride, molybdenum nitride, and vanadium nitride. Examples of conductive metal oxide materials include molybdenum oxide, indium tin oxide, tin oxide, ruthenium oxide, and zinc oxide.

In step 1104, the refractive index (n) and the extinction coefficient (k) are measured at a single wavelength using a single wavelength ellipsometer. In step 1106, the resistivity of the film is determined (e.g. by using a 4-point probe). In step 1108, the constant "X" (e.g. from Eqn. 7) is calculated at the single wavelength using the measured values of n, k, and ρ. In step 1110, the refractive index at different wavelengths between 500 nm and 1000 nm is calculated by substitution into Eqn. 7, thereby allowing the entire spectrum to be determined from measurement at a single wavelength.

Although the foregoing examples have been described in some detail for purposes of clarity of understanding, the invention is not limited to the details provided. There are many alternative ways of implementing the invention. The disclosed examples are illustrative and not restrictive.

What is claimed:

1. A method for determining the refractive index spectrum of a conductive thin film, the method comprising:
depositing the conductive thin film on a substrate;
measuring a refractive index (n) and an extinction coefficient (k) of the conductive thin film at a single wavelength (ω, where ω=c/λ);
measuring a resistivity (ρ) of the conductive thin film;
solving the expression $$n \approx \frac{\rho}{X\omega^3 k}$$

for the constant "X" at the single wavelength; and
calculating the refractive index at a plurality of wavelengths ($\omega_n$) between 500 nm and 1000 nm using the expression $$n \approx \frac{\rho}{X\omega_n^3 k}.$$

2. The method of claim 1 wherein the thin film comprises one of metals, conductive metal nitrides or conductive metal oxides.

3. The method of claim 2 wherein the metals comprises at least one of silver, titanium, tantalum, platinum, ruthenium, nickel, or tungsten.

4. The method of claim 2 wherein the conductive metal nitrides comprises at least one of titanium nitride, tantalum nitride, tungsten nitride, molybdenum nitride, or vanadium nitride.

5. The method of claim 2 wherein the conductive metal oxides comprises at least one of molybdenum oxide, indium tin oxide, tin oxide, ruthenium oxide, and zinc oxide.

6. The method of claim 1 wherein the thin film has a thickness between 100 Å and 3000 Å.

7. A method for predicting a second refractive index of a conductive thin film given a first refractive index of the conductive thin film, the method comprising:
depositing the conductive thin film on a substrate;
measuring a first refractive index ($n_1$) and a first extinction coefficient (k) of the conductive thin film at a first wavelength ($\omega_1$ where $\omega_1 = c/\lambda_1$);
measuring a resistivity (ρ) of the conductive thin film;
solving the expression $$n_1 \approx \frac{\rho}{X\omega_1^3 k}$$

for the constant "X" at the first wavelength; and
predicting the refractive index at a second wavelength ($\omega_2$) by solving the expression $$n_2 \approx \frac{\rho}{X\omega_2^3 k}.$$

8. The method of claim 7 wherein the predicting is repeated at a plurality of wavelengths ($\omega_n$) between 500 nm and 1000 nm.

9. The method of claim 8 wherein the thin film comprises one of metals, conductive metal nitrides or conductive metal oxides.

10. The method of claim 9 wherein the metals comprises at least one of silver, titanium, tantalum, platinum, ruthenium, nickel, or tungsten.

11. The method of claim 9 wherein the conductive metal nitrides comprises at least one of titanium nitride, tantalum nitride, tungsten nitride, molybdenum nitride, or vanadium nitride.

12. The method of claim 9 wherein the conductive metal oxides comprises at least one of molybdenum oxide, indium tin oxide, tin oxide, ruthenium oxide, and zinc oxide.

13. The method of claim 7 wherein the thin film has a thickness between 100 Å and 3000 Å.

* * * * *